United States Patent

Dunn et al.

(10) Patent No.: US 6,284,769 B1
(45) Date of Patent: Sep. 4, 2001

(54) NONPEPTIDE KAPPA OPIOID RECEPTOR ANTAGONISTS

(75) Inventors: William Dunn, Oak Park, IL (US); Ludwig Bauer, Las Vegas, NV (US); Hemendra N. Bhargava, Punjab (IN)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/454,670

(22) Filed: Dec. 3, 1999

(51) Int. Cl.[7] ................ A61K 31/485; C07D 489/08; A61P 25/04
(52) U.S. Cl. .................. 514/279; 546/39; 546/40
(58) Field of Search .................. 546/39, 40; 514/279

(56) References Cited

U.S. PATENT DOCUMENTS

| | | | |
|---|---|---|---|
| 4,649,200 | 3/1987 | Portoghese et al. | 546/26 |
| 4,889,860 | 12/1989 | Rzeszotarski et al. | 514/282 |
| 5,013,739 | 5/1991 | Bihari et al. | 514/282 |
| 5,025,018 | 6/1991 | Faden | 514/277 |
| 5,189,064 | 2/1993 | Blum et al. | 514/561 |
| 5,250,542 | 10/1993 | Cantrell et al. | 514/315 |
| 5,352,680 | 10/1994 | Portoghese et al. | 514/279 |
| 5,457,208 | 10/1995 | Portoghese et al. | 546/35 |
| 5,733,881 | 3/1998 | Schiller | 514/18 |
| 5,837,720 | 11/1998 | Ito | 514/343 |
| 5,945,443 | 8/1999 | Kruse et al. | 514/429 |

OTHER PUBLICATIONS

Protoghese et al., *Life Sci.*, 40, pp. 1287–1292 (1987).
Aldrich, *Burger's Medicinal Chemistry and Drug Discovery*, vol. 3, Wolff, M.E., ed., John Wiley, 5th ed., pp. 321–439 (1996).
Wan et al., *J. Med. Chem.*, 42, pp. 3011–3013 (1999).
Ananthan et al., "Synthesis, opioid receptor binding, and biological activities of naltrexone–derived pyrido–and pyrimidomorphinans," *J. Med. Chem.*, 42, pp. 3527–3538 (1999).
Stroetmann et al. Pharmazie 53, 87–90, 1998.*

Lester et al. Tetrahedron 20 (6), 1407–1417, Jun. 1964.*

* cited by examiner

*Primary Examiner*—Evelyn Mei Huang
(74) *Attorney, Agent, or Firm*—Marshall, O'Toole, Gerstein, Murray & Borun

(57) ABSTRACT

The compounds of structural formulae (I) and (II)

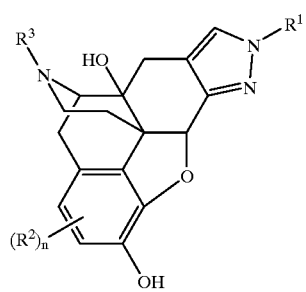

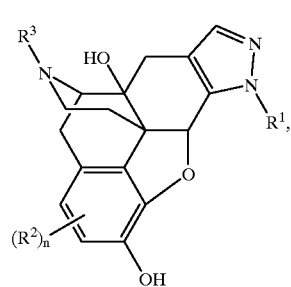

and use of the compounds and salts and hydrates thereof, as therapeutic agents, is disclosed. A compound of formula (I) or (II) is an agonist for the $\mu$ and $\delta$ opioid receptors, an antagonist for the $\kappa$ opioid receptor, and has high affinity at all three receptors. A compound of formula (I) or (II) has utility in a variety of therapeutic and research areas where $\kappa$ opioid receptor antagonism is beneficial, including the treatment of opiate addiction or pain, or in a method of stimulating an immune system of a human.

19 Claims, No Drawings

NONPEPTIDE KAPPA OPIOID RECEPTOR ANTAGONISTS

This invention was made with the assistance of the Government under a grant from the National Institutes of Health (Grant No. DA-08867). The U.S. Government has certain rights in the invention.

BACKGROUND OF THE INVENTION

1. Field of the Invention

The present invention generally relates to novel opioid receptor-active compounds and their pharmaceutically acceptable salts, to methods of preparing the compounds, to pharmaceutical compositions containing the compounds, and to their use as opioid receptor-active agents. These compounds and compositions have utility in a variety of therapeutic areas, including use as nonaddictive analgesics and in a treatment for opiate addiction.

2. Brief Description of Related Technology

Opiates are well known for their usefulness in the treatment of a variety of maladies. Opiates, such as morphine, are potent analgesics, but their usefulness is limited because of adverse side effects, such as physical addictiveness and withdrawal properties. Morphine and related opiates also exhibit other adverse side effects, such as respiratory depression, mood changes, and decreased intestinal motility with concomitant constipation, nausea, vomiting, and alterations in the endocrine and autonomic nervous systems.

Opiates exert their effects by interacting with high-affinity opioid receptors. The opioid receptor was one of the first human receptors hypothesized, and, later, demonstrated to exist in mammalian brain. Three types of opioid receptors have been proposed, and are now widely referred to as the $\mu$, $\delta$ and $\kappa$ types. Subtypes of each type of opioid receptor also have been proposed.

Considerable research has been directed to the opioid receptors, for example, to determine their distinct pharmacological profiles, anatomical distributions, and functions. In particular, it is known that opioid receptors are G-protein coupled receptors, and that they are widely distributed in mammalian systems, both in the central nervous system and in the periphery. See, for example, J. V. Aldrich in *Burger's Medicinal Chemistry and Drug Discovery*, Vol. 3, M. E. Wolff, Ed., John Wiley, Fifth Ed., p. 321–439 (1996).

The $\delta$ opioid receptors are abundant in the central nervous system and play a role in spinal analgesia, gastrointestinal motility, and various hormonal functions. See, for example, R. Spanagel et al., *J. Neurochem.*, 55, p. 1743–50 (1990). Cells of the immune system also have been shown to have $\delta$ opioid receptors on their surface. See, for example, D. J. J. Carr et al., *Cell Immunol.*, 116, p. 44–51 (1988). Thus, immune response is stimulated by $\delta$ opioid receptor agonists (see, for example, S. Mazumder et al., *Immunol. Lett.*, 35, p. 33–38 (1993)), and suppressed by $\delta$ opioid receptor antagonists (see, for example, K. Arakawa et al., *Transplantation*, 53, p. 951–53 (1992)).

The $\mu$ opioid receptors bind morphine-like drugs and mediate opiate phenomena associated with morphine, including analgesia, euphoria, cardiovascular and respiratory functions, and physical dependence. See, for example, K. A. Sporer, *Ann. Int. Med.*, 130, p. 584–90 (1999), and D. J. Nutt, *The Lancet*, 347, p. 31–36 (1996).

The $\kappa$ opioid receptors are widely distributed in the central and peripheral nervous systems, and mediate a spectrum of functions including the modulation of drinking, water balance, food intake, gut motility, temperature control, and various endocrine functions.

The following structure is the morphinone structure that has demonstrated opioid receptor activity. The numbers 6, 7, and 17 designate various important ring positions of the morphinone structure. Oxymorphone, a

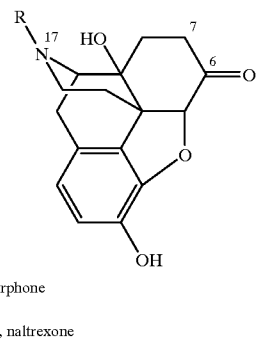

R = CH₃— , oxymorphone

R = ▷—CH₂— , naltrexone morphinone wherein R is methyl, is a nonselective agonist for the $\mu$, $\delta$ and $\kappa$ opioid receptors, and has been used to design a series of fused heterocyclic derivatives at the 6,7 positions. Naltrexone, a morphinone wherein R is cyclopropylmethyl, is a nonselective antagonist of moderate to high affinity for the $\mu$, $\delta$ and $\kappa$ opioid receptors, and also has served as a template for derivatization at the 6,7-positions.

Compounds that act as $\kappa$ opioid receptor antagonists have been discovered only recently. A peptide derivative of dynorphin A-(1–11) recently has been reported to be a $\kappa$ opioid receptor antagonist. See Q. Wan et al., *J. Med. Chem.*, 42, p. 3011 (1999). The compound norBNI is a nonpeptide $\kappa$ opioid receptor antagonist of moderate selectivity. See P. S. Portoghese et al., *Life Sci.*, 40, p. 1287–92 (1987). A nonselective $\kappa$ opioid receptor antagonist is [(−)-(1R,5R,9R)-(5,9-diethyl-2-(3-furylmethyl)-2'-hydroxy-6,7-benzomorphan], reported by J. V. Aldrich in *Burger's Medicinal Chemistry and Drug Discovery*, Vol. 3, M. E. Wolff Ed., John Wiley, Fifth Ed., p. 321–439 (1996).

Because $\kappa$ opioid receptor antagonists have been investigated only recently, insufficient information exists with respect to structure-activity relationships of $\kappa$ opioid receptor antagonists. However, it is known that the 17-N-methyl morphinan derivatives are agonists, while the 17-N-cyclopropylmethyl morphinan derivatives are antagonists.

The pharmacological effects of $\kappa$ opioid receptor agonists and antagonists only now are being investigated. It is known that $\kappa$ opioid receptors, when stimulated, can produce analgesia. See, for example, R. Spanagel et al., *J. Neurochem.*, 55, p. 1743–50 (1990). However, it has recently been reported that one $\kappa$ opioid receptor agonist increased pain when used as a postoperative analgesic. See H. Machelska et al., *J. Pharmcol. Exptl. Therap.*, 290, p. 354–61 (1999). Kappa opioid receptor agonists also have been shown to reduce blood pressure in rats. See M. M. McConnaughey et al., *J. Pharm. Pharmacol.*, 50, p. 1121–25 (1998). One $\kappa$ opioid receptor antagonist has been shown to reduce significantly the self-administration of cocaine in mice, therefore suggesting involvement of the endogenous $\kappa$ opioid receptor system in the mechanisms of self-administration of cocaine. See A. V. Kuzmin et al., *Eur. J. Pharmacol.*, 358, p. 197–202 (1998).

Accordingly, a continuing need exists for compounds and combinations of compounds that act as agonists or antagonists at the μ, δ and κ type opioid receptors, or at the subtypes of these receptors. It also would be desirable to provide compounds or a combination of compounds that exhibit potent analgesic effects without demonstrating the addictive and withdrawal properties associated with present nonpeptide opioid analgesics.

SUMMARY OF THE INVENTION

One aspect of the present invention is to provide a class of opioid receptor-active compounds having structural formulae (I) and (II). These opioid-receptor active compounds are morphinone derivatives. The present morphinone derivatives have a nitrogen-containing heterocyclic group fused to the 6,7-positions of the morphinan system. By introducing a fused, heterocyclic group to the morphinone derivatives, parameters such as hydrogen bonding potential, pKa, and lipophilicity can be varied to optimize opioid receptor affinity and selectivity.

The compounds of formulae (I) and (II) have the structures

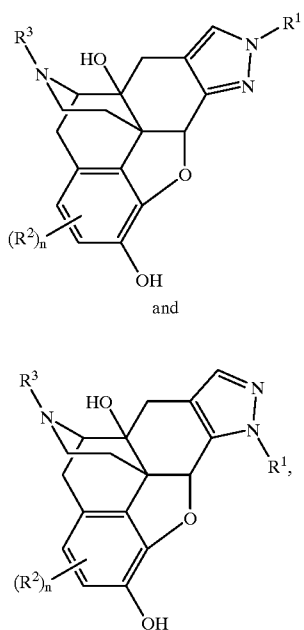

wherein $R^1$ is selected from the group consisting of hydrogen, $C_{1-6}$alkyl, $C_{2-6}$alkenyl, $C_{1-3}$alkylenearyl (i.e., alkaryl), $C_{3-8}$cycloalkyl, $C_{1-3}$alkylene $C_{3-8}$cycloalkyl, $C_{1-3}$alkylene $C_{3-8}$heterocycloalkyl, $C_{3-8}$heterocycloalkyl, aryl, and aryl$C_{1-3}$alkyl (i.e., aralkyl);

$R^2$, independently, is selected from the group consisting of halo, $CF_3$, $C_{1-6}$alkyl, $C_{3-8}$cycloalkyl, $C(=O)OR^a$, $OR^a$, and $C_{1-3}$alkylene $C_{3-8}$cycloalkyl;

$R^3$ is selected from the group consisting of hydrogen, $C_{1-6}$alkyl, $C_{2-6}$alkenyl, and $C_{2-6}$alkynyl;

$R^a$, independently, is selected from the group consisting of hydrogen, $C_{1-6}$alkyl, $C_{3-8}$cycloalkyl, $C_{1-4}$alkyleneC(=O)OR$^b$, aryl, aryl$C_{1-3}$alkyl, $C_{1-3}$alkylenearyl, and Het;

$R^b$ is selected from the group consisting of hydrogen, $C_{1-6}$alkyl, aryl, aryl$C_{1-3}$alkyl, $C_{1-3}$alkylenearyl, and Het;

Het is a 5- or 6-membered heterocyclic group, saturated or partially or fully unsaturated, containing at least one heteroatom selected from the group consisting of oxygen, nitrogen, and sulfur, and optionally substituted with $C_{1-4}$alkyl;

n is an integer 0, 1, or 2;

and pharmaceutically acceptable salts and hydrates thereof.

Another aspect of the present invention is to provide methods of preparing the compounds of formulae (I) and (II) and their pharmaceutically acceptable salts.

Yet another aspect of the invention is to provide pharmaceutical compositions containing a compound of formulae (I) or (II), or their pharmaceutically acceptable salts, and to the use of such compositions in the treatment of conditions wherein a κ receptor antagonist provides a benefit.

An additional aspect of the invention is to provide compounds of formulae (I) and (II), and their pharmaceutically acceptable salts, for use in the treatment of conditions in which agonism at the μ and δ opioid receptors, and antagonism at the κ opioid receptor, provides a benefit.

A further aspect of the present invention is to provide compounds of formula (I) and (II), and their pharmaceutically acceptable salts, for use as analgesics or as immune system stimulants, or for use in the treatment of opiate addiction or in the characterization of other investigative opioid receptor-active agents.

Another aspect of the present invention is the use of compound of formula (I) or (II) in the manufacture of a medicament, such as an analgesic or an immune system stimulant, or for use in the treatment of opiate addiction.

Still another aspect of the present invention is to provide a method of treating opiate addiction, pain, or a suppressed immune system in a human or non-human animal body comprising administering to said body a therapeutically effective amount of a compound of formula (I) or (II).

Further aspects and advantages of the invention will become apparent to those skilled in the art from a review of the following detailed description, taken in conjunction with the appended claims. It should be noted, however, that while the invention is susceptible of embodiments in various forms, described hereinafter are specific embodiments of the invention with the understanding that the present disclosure is intended as illustrative, and is not intended to limit the invention to the specific embodiments described herein.

DETAILED DESCRIPTION OF THE PREFERRED EMBODIMENTS

The present invention is directed to a class of opioid receptor-active morphinans and their pharmaceutically acceptable salts and hydrates, to methods of preparing the compounds, to pharmaceutical compositions containing the compounds, and to their therapeutic use as opioid receptor-active agents.

In particular, the opioid receptor-active morphinans have the structural formulae (I) or (II), and generally are morphinone derivatives having a heterocyclic pyrazole group fused to the 6,7-positions of the morphinan system.

The compounds of formulae (I) and (II) have the structures

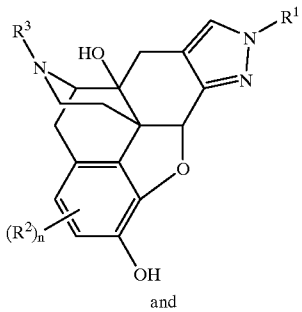

(I)

and

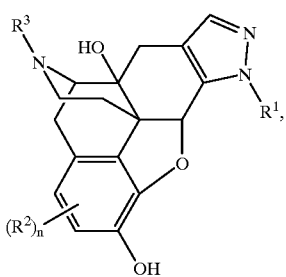

(II)

wherein $R^1$ is selected from the group consisting of hydrogen, $C_{1-6}$alkyl, $C_{2-6}$alkenyl, $C_{1-3}$alkylenearyl (i.e., alkaryl), $C_{3-8}$cycloalkyl, $C_{1-3}$alkyleneC$_{3-8}$cycloalkyl, $C_{1-3}$alkyleneC$_{3-8}$heterocycloalkyl, $C_{3-8}$heterocycloalkyl, aryl, and aryl$C_{1-3}$alkyl (i.e., aralkyl);

$R^2$, independently, is selected from the group consisting of halo, $CF_3$, $C_{1-6}$alkyl, $C_{3-8}$cycloalkyl, $C(=O)OR^a$, $OR^a$, and $C_{1-3}$alkyleneC$_{3-8}$cycloalkyl;

$R^3$ is selected from the group consisting of hydrogen, $C_{1-6}$alkyl, $C_{2-6}$alkenyl, and $C_{2-6}$alkynyl;

$R^a$, independently, is selected from the group consisting of hydrogen, $C_{1-6}$alkyl, $C_{3-8}$cycloalkyl, $C_{1-4}$alkyleneC(=O)OR$^b$, aryl, aryl$C_{1-3}$alkyl, $C_{1-3}$alkylenearyl, and Het;

$R^b$ is selected from the group consisting of hydrogen, $C_{1-6}$alkyl, aryl, aryl$C_{1-3}$alkyl, $C_{1-3}$alkylenearyl, and Het;

Het is a 5- or 6-membered heterocyclic group, saturated or partially or fully unsaturated, containing at least one heteroatom selected from the group consisting of oxygen, nitrogen, and sulfur, and optionally substituted with $C_{1-4}$alkyl;

n is an integer 0, 1, or 2;

and pharmaceutically acceptable salts and hydrates thereof.

The term "alkyl" or "alkylene" as used herein is a hydrocarbon group containing the indicated number of carbon atoms and includes straight chained and branched alkyl or alkylene groups, typically methyl, methylene, ethyl, ethylene, and straight chain and branched propyl, propylene, butyl, and butylene groups. The terms "alkenyl" and "alkynyl" as used herein have definitions identical to "alkyl," except for the presence of at least one site of carbon-carbon double bond or triple bond unsaturation in the carbon chain.

Similarly, the term "cycloalkyl" as used herein contains the indicated number of carbon atoms forming an aliphatic ring structure. The term "heterocycloalkyl" is similarly defined, except that one to three of the carbon atoms in the aliphatic ring have been substituted with one to three heteroatoms independently selected from the group consisting of oxygen, nitrogen, and sulfur, e.g., morpholinyl, piperidyl, pyrrolidinyl, and piperazinyl.

The term "halo" or "halogen" as used herein includes fluorine, bromine, chlorine, and iodine groups. "$CF_3$" is trifluoromethyl.

The term "aryl" as used herein refers to optionally substituted 5- or 6-membered carbocyclic and heterocyclic aromatic groups, including, but not limited to, phenyl, thienyl, furyl, pyrryl, imidazolyl, pyrimidyl, and pyridyl.

The terms "$C_{1-3}$alkylenearyl" and "alkaryl" as used herein refer to an alkylene chain containing the indicated number of carbon atoms and having an aryl substituent, e.g., benzyl. The terms "aryl$C_{1-3}$alkyl" and "aralkyl" as used herein refer to an aryl group having a $C_{1-3}$ alkyl substituent, e.g., ethylphenyl. The term "$C_{1-3}$alkyleneC$_{3-8}$cycloalkyl" is similarly defined as an alkylene group containing a cycloalkyl substituent, e.g., cyclopropylmethyl.

Various abbreviations used herein are defined as follows: °C. is degree centigrade; OAc is acetate or $O-C(=O)CH_3$; Et is ethyl or $C_2H_5$; g is gram; hr is hour or hours; $K_i$ is equilibria constant; L is liter; μL is microliter; M is molar or moles per liter; Me is methyl or $CH_3$; mg is milligram; min is minute; mL is milliliter; mmol is millimoles; mp is melting point; "NMR" or "nmr" is nuclear magnetic resonance spectroscopy; and negative numbers are indicated with a hyphen or "-" before the number.

When $R^1$ is hydrogen, the compounds of formulae (I) and (II) can exist in tautomeric forms, and the invention includes both mixtures and separate individual tautomers thereof.

The pharmaceutically acceptable salts of the compounds of formulae (I) and (II) are acid addition salts formed with pharmaceutically acceptable acids. Examples include the hydrochloride, hydrobromide, sulphate, bisulphate, phosphate, hydrogen phosphate, acetate, benzoate, succinate, fumarate, maleate, lactate, citrate, tartrate, gluconate, methanesulphonate, benzenesulphonate and p-toluenesulphonate salts.

In one preferred embodiment, $R^1$ of compounds of formula (I) or (II) is hydrogen.

In another preferred embodiment, n is 0 or $R^2$ of compounds of formula (I) or (II) is halogen, especially fluorine.

In a further preferred embodiment, $R^3$ of compounds of formula (I) or (II) is $C_{1-6}$alkyl, especially $C_{1-3}$alkyl, and most preferably methyl.

Particular individual compounds of the present invention include:

17-Methyl-6,7-dehydro-3,14-hydroxy-4,5α-epoxy-6,7:5',4'(6,7:3',4')-pyrazolomorphinan, and 17-Methyl-6,7-dehydro-3,14-hydroxy-4,5α-epoxy-6,7:5',4'(6,7:3',4')-pyrazolomorphinan dihydrochloride.

Compounds of the present invention have moderate to high affinity for the μ, δ and κ type opioid receptors. The compounds may have partial selectivity for the μ type opioid receptor over the δ and κ type opioid receptors. Surprisingly, compounds of the present invention are agonists for the μ and δ opioid receptors, but are antagonists for the κ opioid receptor. Thus, as antagonists, the compounds are inhibitors of κ opioid receptor function. The compounds of formulae (I) and (II) can be used in therapy, particularly for use in the treatment of a variety of conditions where κ opioid receptor antagonism is considered to be beneficial, and especially where μ and δ opioid receptor agonism also is beneficial.

As κ opioid receptor antagonists and μ and δ opioid receptor agonists, the compounds of the present invention exhibit a pharmacological profile that meets the target of the Opiate Treatment Discovery Program of NIH. The compounds of formulae (I) and (II) therefore have utility as analgesics, without exhibiting the addictive or withdrawal properties associated with currently used nonpeptide opioid analgesics. The compounds of formulae (I) and (II) also have utility in the treatment of opiate addiction or as immune system stimulants. The present compounds further provide a method of selectively blocking κ opioid receptors in mammalian tissue comprising the step of contacting said receptors, in vivo or in vitro, with an effective blocking amount of a compound of formula (I) or (II), preferably in conjunction with a pharmaceutically acceptable carrier. The compounds of formulae (I) and (II) also can be used as pharmacological and biochemical probes for use in characterizing the structure and function of other opioid receptor-active agents.

It should be appreciated that references herein to treatment extend to prophylaxis as well as treatment of established conditions. It should also be appreciated that a compound of formula (I) or (II), or a physiologically acceptable salt or hydrate thereof, can be administered as the neat compound, or as a pharmaceutical composition containing such entities.

Compounds of the invention can be administered by any suitable route, for example by oral, buccal, sub-lingual, rectal, vaginal, nasal, topical, or parenteral (including intrathecal, intracerebroventricular, intravenous, intramuscular, subcutaneous and intracoronary) administration. Oral and parenteral, administration are generally preferred, in the form of a pharmaceutical unit dosage form comprising the active ingredient in combination with a pharmaceutically acceptable carrier, which may be a solid, semi-solid, or liquid diluent, or an ingestible capsule or tablet. Usually, the active substance comprises about 0.05% to about 99%, preferably about 0.1% to about 95%, by total weight of the pharmaceutical unit dosage form, for example, about 0.5% to about 20% by weight of a preparation intended for injection or infusion, and about 0.1% to about 50% of a preparation, such as tablets or capsules, intended for oral administration.

Compounds and pharmaceutical compositions suitable for use in the present invention include those wherein the active ingredient is administered in an amount effective to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

The amount of composition administered is dependent on the subject being treated, on the subject's weight, the severity of the affliction, the manner of administration, and the judgment of the prescribing physician. Specifically, for administration to a human in the curative or prophylactic treatment of the conditions and disorders identified above, oral dosages of a compound of formula (I) or (II) generally are about 0.5 to about 1000 mg daily for an average adult patient (70 kg). Thus, for a typical adult patient, individual tablets or capsules contain about 0.2 mg to about 500 mg of active compound, in a suitable pharmaceutically acceptable vehicle or carrier, for administration in single or multiple doses, once or several times per day.

Dosages for intravenous, buccal, or sublingual administration typically are about 0.1 mg to about 500 mg per single dose as required. In practice, the physician determines the actual dosing regimen which is most suitable for an individual patient, and the dosage varies with the age, weight, and response of the typical patient. The above dosages are exemplary of the average case, but there can be individual instances in which higher or lower dosages are merited, and such are within the scope of this invention.

For human use, a compound of formula (I) or (II) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formulae (I) and (II) into preparations which can be used pharmaceutically.

For example, the compound can be administered orally, buccally, or sublingually, in the form of tablets containing excipients such as starch or lactose, or in capsules or ovules either alone or in admixture with excipients, or in the form of elixirs or suspensions containing flavoring or coloring agents. Such liquid preparations can be prepared with pharmaceutically acceptable additives, such as suspending agents (e.g., methylcellulose, a glyceride, or mixtures of glycerides such as a mixture of apricot kernel oil and PEG-6 esters, or mixtures of PEG-8 and caprylic/capric glycerides). A compound also can be injected parenterally, for example, intrathecally, intracerebroventricularly, intravenously, intramuscularly, subcutaneously, or intracoronarily. For parenteral administration, the compound typically is used in the form of a sterile aqueous solution which can contain other substances, for example, salts, or monosaccharides, such as mannitol or glucose, to make the solution isotonic with blood.

For veterinary use, a compound of formula (I) or (II) or a nontoxic salt thereof, is administered as a suitably acceptable formulation in accordance with normal veterinary practice. The veterinarian can readily determine the dosing regimen and route of administration that is most appropriate for a particular animal.

Thus, a pharmaceutical composition comprising a compound of formula (I) or (II), together with a pharmaceutically acceptable diluent or carrier therefor, can be prepared by practices well known in the art. For example, a process of preparing a pharmaceutical composition containing a compound of formula (I) or (II) comprises admixing a compound of formula (I) or (II) with a pharmaceutically acceptable diluent or carrier therefor.

In one embodiment, the pharmaceutical composition is used as an analgesic or an immune system stimulant, said composition comprising a compound of formula (I) or (II), or a pharmaceutically acceptable salt or hydrate thereof, together with a pharmaceutically acceptable diluent or carrier. In another embodiment, the composition is used in the treatment of opiate addiction.

A compound of formula (I) or (II) also can be used in combination with other therapeutic agents useful in the treatment of the above-mentioned and other disease states. The invention thus provides, in another aspect, a combination of a compound of formula (I) or (II), together with a second therapeutically active agent, for use in treating a disease or condition.

For example, a compound of formula (I) or (II) can be used in the preparation of a medicament for co-administration with the second therapeutically active agent in treatment of conditions where antagonism at the κ opioid receptor is beneficial. In addition, a compound of formula (I) or (II) can be used in the preparation of a medicament for use as adjunctive therapy with a second therapeutically active compound to treat such conditions. Appropriate doses of known second therapeutic agents for use in combination with a compound of formula (I) or (II) are readily appreciated by those skilled in the art.

The combination referred to above conveniently can be presented for use in the form of a pharmaceutical formulation, and thus pharmaceutical compositions comprising a combination as defined above together with a pharmaceutically acceptable diluent or carrier comprise a further aspect of the invention. The individual components of such a combination also can be administered either sequentially or simultaneously in separate pharmaceutical formulations.

Compounds of formulae (I) and (II) and their pharmaceutically acceptable salts can be prepared by any suitable method known in the art, or by the following process which forms part of the present invention. In the method below, $R^1$, $R^2$, and $R^3$ are as defined above unless otherwise indicated.

Thus, a process for preparing a compound of the formula (I) or (II) comprises methylating a compound of structural formula (III) with

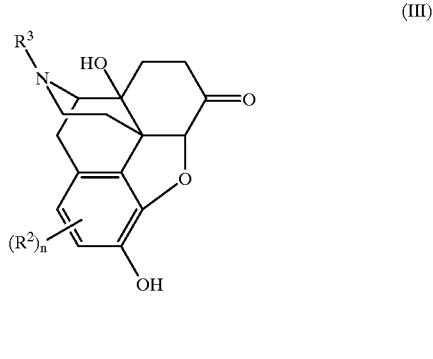

(III)

trimethylsilyldiazomethane (see A. Toyohiko et al., *Chem. Pharm. Bull.*, 32, p. 3759–63 (1984)), to give a 3-O-methyl ether having a structural formula (IV).

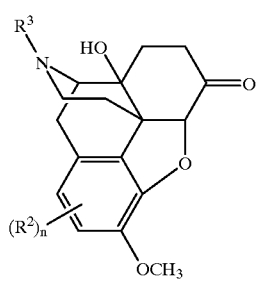

(IV)

A compound of structural formula (IV) can be converted to an enaminone of formula (V) by refluxing the 3-O-methyl ether (IV) in dimethylformamide dimethyl acetal (DMF-DMA) (see M. P. Kotick et al., *J. Med. Chem.*, 24, p. 1445–50 (1981)).

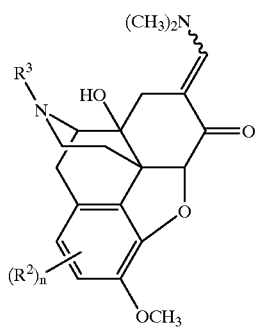

(V)

The enaminone is then transformed to the pyrazolo derivatives of structural formulae (VI) and (VII)

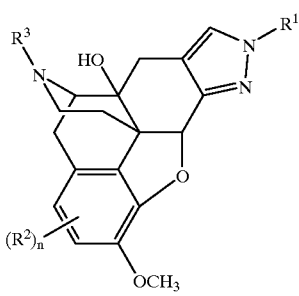

(VI)

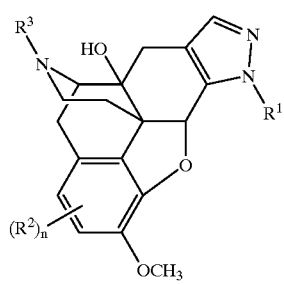

(VII)

by reaction with an appropriate hydrazine, $R^1NH-NH_2$, wherein $R^1$ has previously been defined. Deprotection of the phenol with boron tribromide provides a mixture of the 1'- and 2'-substituted pyrazolo derivatives of formulae (I) and (II), which are separated by chromatography to give the desired isomers of formulae (I) and (II).

The pharmaceutically acceptable acid addition salts of the compounds of formulae (I) and (II) can be prepared in a conventional manner. For example, a compound of structural formula (I) or (II) can be treated with a suitable acid, either neat or in a suitable solution, and the resulting salt can be isolated either by filtration or by evaporation of the reaction solvent under vacuum. The salts also can be formed, or interconverted, using ion-exchange resin techniques. In addition, compounds of structural formulae (I) and (II) can be isolated in association with solvent molecules (e.g., water or other solvates) by crystallization from, or evaporation of, an appropriate solvent.

The synthesis of compounds of structural formulae (I) and (II) is illustrated by the following non-limiting examples. $^1$H and $^{13}$C NMR spectra (at 300 MHz and 75.4 MHz, respectively) were obtained in deuterochloroform using a Varian XL-300 spectrometer. Silica gel grade 60 (200 to 400 mesh) was used for column chromatography.

EXAMPLE 1

17-Methyl-6,7-dehydro-3,14-hydroxy-4,5α-epoxy-6, 7:5',4'(6,7:3',4')pyrazolomorphin (tautomers)

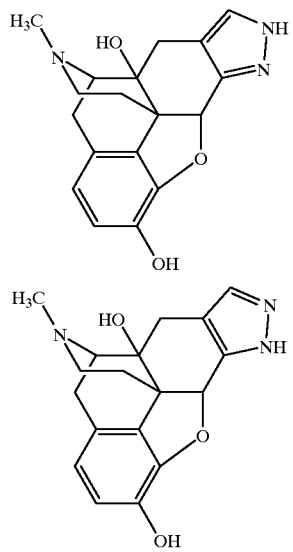

Trimethylsilyldiazomethane (0.65 mL, 1.30 mmol, 2.0 M solution in hexane) was added to a stirred solution of oxymorphone (300 mg, 1.0 mmol) (formula (III) wherein $R^3$ is $CH_3$ and n is 0) and trimethylamine (0.21 mL, 1.50 mmol) in methanol/acetonitrile (MeOH/$CH_3$CN) (1:9, 6.5 mL). The resulting solution was stirred at room temperature for 5 hours. Solvents then were removed in vacuo to yield a yellow residue. The residue was recrystallized from methanol/ethyl acetate (MeOH/EtOAc) to yield colorless crystals of a 3-O-methyloxymorphone, a compound of formula (IV) wherein $R^3$ is $CH_3$ and n is 0. After filtration, the solvent was removed from the filtrate, and the remaining residue was recrystallized from MeOH/EtOAc to yield an additional batch of the colorless 3-O-methyloxymorphone crystals (mp 217° C. to 218° C.). The total yield of product was 260 mg (0.82 mmol, 82%). A mixture of the 3-O-methyloxymorphone (220 mg, 0.698 mmol) and DMF-DMA (1.25 mL) was heated under reflux for 4 hours, and then evaporated to dryness in vacuo. The resulting residue was crystallized from chloroform/ethyl acetate ($CHCl_3$/EtOAc) to yield light yellow crystals of an enaminone of formula (V) wherein $R^3$ is $CH_3$ and n is 0 (200 mg, 77% yield, mp 253° C. to 255° C.). The enaminone (400 mg, 1.08 mmol) was stirred in a MeOH:$H_2O$ solution (4:1, 8 mL) with hydrazine hydrate (665 µL, 13.42 mmol) at reflux for 3 hours. Concentration of the mixture in vacuo provided white crystals which were collected by filtration, washed with water, dried, and then recrystallized from $CHCl_3$-EtOAc to yield the pyrazoles of formula (VI) and (VII) wherein $R^1$ is hydrogen, $R^3$ is $CH_3$, and n is 0 (337 mg, 99% yield based on (V), mp 297° C. to 298° C.). To a stirred, cold (0° C. to 4° C.) solution of the pyrazoles (340 mg, 1 mmol) in anhydrous dichloromethane ($CH_2Cl_2$) was added 5 drops of a 1.0 molar solution of boron tribromide ($BBr_3$) in $CH_2Cl_2$ (10 mmol). The mixture was stirred at room temperature for 2 to 4 hours, cooled to 0° C. to 4° C. in an ice bath, and then neutralized with solid potassium carbonate ($K_2CO_3$) to pH 9. The organic layer was separated and the aqueous layer was extracted with chloroform ($CHCl_3$) or chloroform/2-propanol ($CHCl_3$/iPrOH) (3:1). The combined organic extracts were washed with brine, then dried over sodium sulfate ($Na_2SO_4$). After evaporation of solvents in vacuo, the residue was purified on a short silica gel column to give the titled tautomers.

Analytical: ($C_{18}H_{19}N_3O_3$·$2H_2O$) Calculated: C, 62.31; H, 6.22; N, 12.11.

Found: C, 62.34; H, 5.71; N, 11.84.

EXAMPLE 2

17-Methyl-6,7-dehydro-3,14-hydroxy-4,5α-epoxy-6, 7:5',4'(6,7:3',4')-pyrazolomorphinan dihydrochloride Hydrogen chloride (5 mmol, 1 M solution in diethyl ether) was added to a stirred cold (0° C. to 4° C.) solution of the compounds of Example 1 (1 mmol) in dichloromethane-methanol. The mixture was stirred for 10 minutes, then evaporated to dryness in vacuo to give a pure salt in quantitative yield ($^1$H NMR).

Analytical: ($C_{18}H_{19}N_3O_3$·2HCl·$H_2O$) Calculated: C, 51.93; H, 5.57; N, 10.09.

Found: C, 52.02; H, 5.56; N, 10.00.

EXAMPLE 3

Opioid Receptor Activities

Opioid receptor activity studies were carried out by the method of the Opiate Treatment Discovery Program of the National Institutes of Health. Receptor binding studies were conducted on Chinese hamster ovary (CHO) cells which had been transfected with human DNA encoding for the µ, δ, and κ opiate receptors, respectively.

The cell line expressing the µ opioid receptor is maintained in Ham's F-12 medium supplemented with 10% fetal bovine serum and 400 µg/ml GENETICIN (G418 sulfate). The cell line expressing the δ opioid receptor is maintained in Ham's F-12 medium supplemented with 10% fetal bovine serum and 500 µg/ml hygromycin B. The cell line expressing the κ opioid receptor is maintained in Dulbecco's minimal essential medium (DMEM) supplemented with 10% fetal bovine serum, 400 µg/ml GENETICIN (G418 sulfate), and 0.1% penicillin/streptomycin. All cell lines are grown to full confluency, then harvested for membrane preparation. The membrane used for functional assays is prepared in buffer A (20 mM HEPES, 10 mM $MgCl_2$, and 100 mM NaCl at pH 7.4) and the membrane for binding assays is prepared in 50 mM Tris buffer, pH 7.7. Cells are harvested by scraping the plates with a rubber policeman and then centrifuged at 500 times gravity for 10 minutes. The cell pellet is suspended in buffer A or Tris buffer, homogenized in a Polytron Homogenizer, and centrifuged at 20,000 times gravity for 20 minutes. The cell pellet is washed in buffer A or Tris, centrifuged at 20,000 times gravity for another 20 minutes, and, finally, suspended in a small amount of buffer to determine protein content. Membrane is aliquoted in small vials at a concentration of 6 mg/ml per vial, stored at −70° C., and used as needed.

Binding assays were conducted using [$^3$H]DAMGO, [$^3$H]Cl-DPDPE and [$^3$H]U69,593 as labelling ligands specific for µ, δ and κ opioid receptors, respectively. DAMGO is Tyr-D-Ala-Gly-NMePhe-NHCH$_2$OH. The structural formulae for U69,593 and Cl-DPDPE are

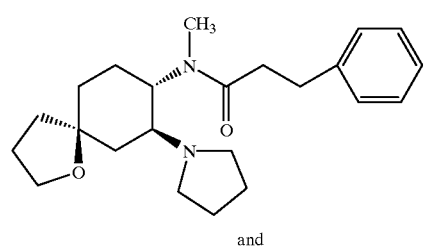

U69,593 and

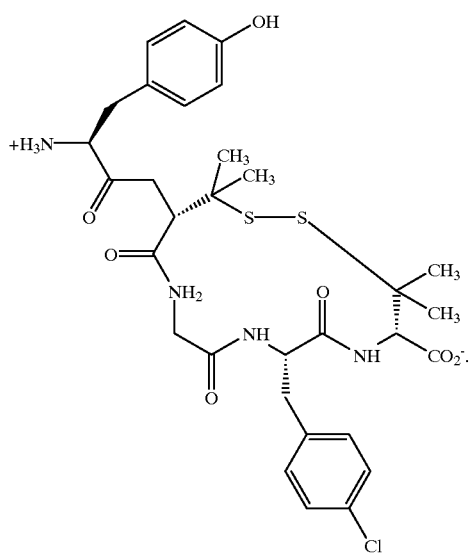

Cl-DPDPE

Cell membranes were incubated with the appropriate radioligand and unlabeled compounds of Example 1 in a total volume of 200 µl in 96-well plates, usually for 1 hour at 25° C. Membranes were incubated with the compounds of Example 1 at concentrations ranging from $10^{-10}$ to $10^{-5}$ M. After the incubation, samples were filtered through glass fiber filters by using a Tomtec cell harvester. Filters were dried overnight before radioactivity levels were determined. Nonspecific binding was determined by using 1.0 µM of the unlabeled counterpart of each radioligand.

Analysis of the data for $IC_{50}$ values and Hill coefficients was performed using the program PRISM. Opioid receptor binding constants, $K_i$, were calculated using the Cheng-Prusoff transformation, $K_i=IC_{50}/(1+L/K_d)$, where L is radioligand concentration and $K_d$ is the binding affinity of the radioligand, as determined previously by saturation analysis. See Y. C. Cheng et al., Biochem. Pharmacol., 22, p. 3099–3102 (1973). To determine agonist/antagonist properties, membranes prepared as described above were incubated with [$^{35}$S]GTPγS (50 pM), GDP (usually 10 µM) and the compound of Example 1 in a total volume of 200 µl for 60 min at 25° C. Samples were filtered over glass fiber filters and counted as described for the binding assays. A dose response curve with a prototypical full agonist (DAMGO, Cl-DPDPE, and U69593, for µ, δ, and κ, respectively) was conducted to identify full and partial agonist compounds.

Agonist activity at µ, δ and κ receptors is reported as % stimulation relative to the respective agonists DAMGO, Cl-DPDPE, and U69,593. High affinity compounds that demonstrated no agonist activity were tested as antagonists. A full Schild analysis was conducted, utilizing a full agonist dose response curve in the presence of at least three concentrations of the antagonist. $pA_2$ values and Schild slopes were determined using a statistical program designed for these experiments.

The receptor binding data for the compound of Example 1 ($K_i$(SEM)(nM)) is as follows: µ([$^3$H]-DAMGO)=3.75 (0.71); δ([$^3$H]-Cl-DPDPE)=19.06(1.17); κ([$^3$H]-U69,593)= 12.29(6.20). Agonist/antagonist data ($EC_{50}$(nM)(SEM) (% Stimulation)) is as follows: µ-CHO membrane=19.26(0.54) (80.30); δ-CHO membrane=25.02(4.67) (75.20); κ-CHO membrane=$K_e$=59.33(18.85). The $pA_2$ value is 7.29±0.30 and the slope is −0.92±0.32.

This data shows that the tautomers of Example 1 (i.e. the compounds of formulae (I) and (II) wherein $R^1$ and $R^2$ are hydrogen and $R^3$ is $CH_3$) have a high affinity for the three opioid receptors. The compounds have partial selectivity for the µ type opioid receptor over the δ and κ type opioid receptors (about 7 times more affinity for µ over δ and about 7 times more affinity for µ over κ). This compound is an agonist for the µ and δ receptors and an antagonist for the κ receptor. This compound has both hydrogen bond donor and acceptor sites, and the acceptor site is expected to be basic and protonated in aqueous solution.

The compounds of Example 1 also have been shown to have weak stimulatory activity at the δ receptor of the T-cell of the immune system. In vivo testing on rats has shown that the compounds of Example 1 have potent analgesic activity with a long duration of activity.

The foregoing description is given for clearness of understanding only, and no unnecessary limitations should be understood therefrom, as modifications within the scope of the invention will be apparent to those having ordinary skill in the art.

What is claimed is:

1. A compound of formula (I) or (II)

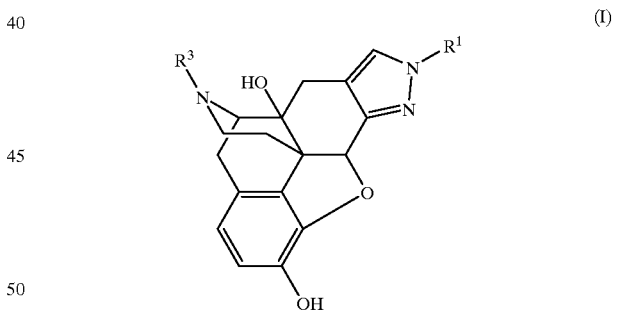

(I)

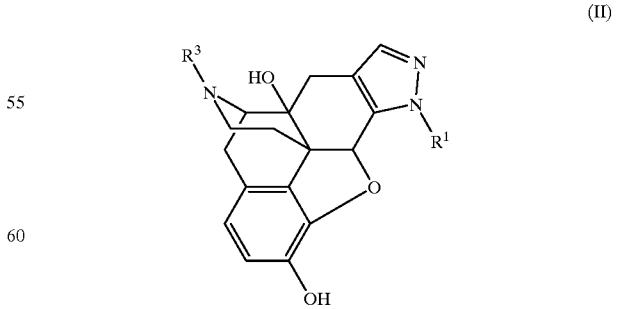

(II)

wherein $R^1$ is selected from the group consisting of hydrogen, $C_{1-6}$alkyl, $C_{2-6}$alkenyl, $C_{3-8}$cycloalkyl, and aryl, and $R^3$ is selected from the group consisting of hydrogen, $C_{1-6}$alkyl, $C_{2-6}$alkenyl, and $C_{2-6}$alkynyl;
a pharmaceutically acceptable salt or hydrate thereof.

2. The compound of claim 1 wherein $R^3$ is cyclopropylmethyl.

3. The compound of claim 1 wherein $R^3$ is cyclopropylmethyl and $R^1$ is hydrogen.

4. The compound of claim 1 wherein $R^1$ is methyl.

5. The compound of claim 1 wherein $R^1$ is methyl and $R^3$ is methyl.

6. The compound of claim 1 wherein $R^1$ is phenyl.

7. The compound of claim 1 wherein $R^1$ and $R^3$ are methyl.

8. A compound having a formula (I) or (II)

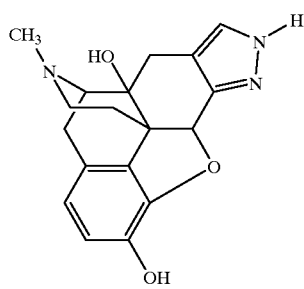

(I)

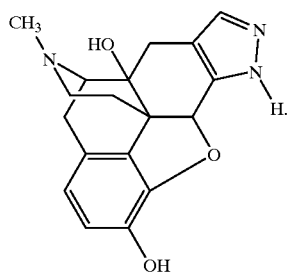

(II)

9. A compound of claim 1 wherein $R^1$ is hydrogen.

10. A compound of claim 1 wherein $R^3$ is $C_{1-6}$alkyl.

11. A compound of claim 10 wherein $R^3$ is $C_{1-3}$alkyl.

12. A compound of claim 11 wherein $R^3$ is methyl.

13. 17-Methyl-6,7-dehydro-3,14-hydroxy-4,5α-epoxy-6,7:5',4'(6,7:3',4')-pyrazolomorphinan, a physiologically acceptable salt or hydrate thereof.

14. A pharmaceutical composition comprising a compound of claim 1 and a pharmaceutically acceptable carrier therefor.

15. A method of treating opiate addiction or pain, in a human or non-human animal body in need thereof, comprising administering to said body a therapeutically effective amount of a compound of claim 1.

16. A method of blocking kappa opioid receptor activity in a human or non-human animal body in need thereof, comprising administering to said body a therapeutically effective amount of a compound of claim 1.

17. The method of claim 16 wherein said compound simultaneously acts as an agonist at the mu and delta opioid receptors.

18. A method of treating a condition in which blocking a kappa opioid receptor is of therapeutic benefit, in a human or nonhuman animal body in need thereof, comprising administering to said body a therapeutically effective amount of a compound of claim 1.

19. A method of treating a human or nonhuman animal in need thereof for a condition where blocking a kappa opioid receptor is of a therapeutic benefit, comprising treating said animal with an effective amount of a pharmaceutical composition comprising a compound of claim 1 together with a pharmaceutical acceptable carrier.

\* \* \* \* \*

UNITED STATES PATENT AND TRADEMARK OFFICE
CERTIFICATE OF CORRECTION

PATENT NO. : 6,284,769 B1
DATED : September 4, 2001
INVENTOR(S) : Dunn et al.

It is certified that error appears in the above-identified patent and that said Letters Patent is hereby corrected as shown below:

Title page,
Item [56], References Cited, OTHER PUBLICATIONS, "Protoghese" should be -- Portoghese --; and "pyrido-and" should be -- pyrido- and --

Column 4,
Lines 13, 18 and 62, "formulae (I) or (II)" should be -- formula (I) or (II) --

Column 11,
Line 6, "pyrazolomorphin" should be -- pyrazolomorphinan --

Column 12,
Line 8, "($C_{18}H_{19}N_3O_3 \cdot .2H_2O$)" should be -- ($C_{18}H_{19}N_3O_3 \cdot 1.2H_2O$) --

Column 13,
Line 63, "U69593" should be -- U69,593 --

Signed and Sealed this

Twenty-ninth Day of July, 2003

JAMES E. ROGAN
*Director of the United States Patent and Trademark Office*